United States Patent [19]
Grundei

[11] Patent Number: 4,711,639
[45] Date of Patent: Dec. 8, 1987

[54] ANCHORAGE FOR TIBIA PLATES

[75] Inventor: Hans Grundei, Lübeck, Fed. Rep. of Germany

[73] Assignee: S+G Implants GmbH, Lubeck, Fed. Rep. of Germany

[21] Appl. No.: 774,577

[22] Filed: Sep. 10, 1985

[30] Foreign Application Priority Data

Sep. 11, 1984 [DE] Fed. Rep. of Germany ....... 3433264

[51] Int. Cl.[4] .............................................. A61F 2/38
[52] U.S. Cl. .................................................... 623/20
[58] Field of Search .............................. 623/20, 16–19, 623/21–23; 128/92 C

[56] References Cited
U.S. PATENT DOCUMENTS

| 4,207,627 | 6/1980 | Cloutier | 623/20 |
| 4,217,666 | 8/1980 | Averill | 623/20 |
| 4,479,271 | 10/1984 | Bolesky et al. | 128/92 C |

FOREIGN PATENT DOCUMENTS 0032828  7/1981  European Pat. Off. ............. 623/20

*Primary Examiner*—Richard J. Apley
*Assistant Examiner*—David J. Isabella
*Attorney, Agent, or Firm*—Balogh, Osann, Kramer, Dvorak, Genova & Traub

[57] ABSTRACT

An anchorage for tibia plates of knee joint endoprostheses which provides for each tibia plate of plastic a metal tray which carries the plate and is provided with one straight planar wall having on the inside surface thereof a T-shaped projection engaging with a T-shaped recess of the tibia plate. The metal tray has another side wall in the form of a circular arc which conically thickens from the top downwards to the base of the tray. The underside of the tray, including the base and lower webs thereof, is provided with a metallic open-cell coating or layer, into the cells of which bone tissue can grow in with subsequent formation of bone, so that the tray always remains joined to the shin bone, while the tibia plate is detachable and exchangeable.

4 Claims, 7 Drawing Figures

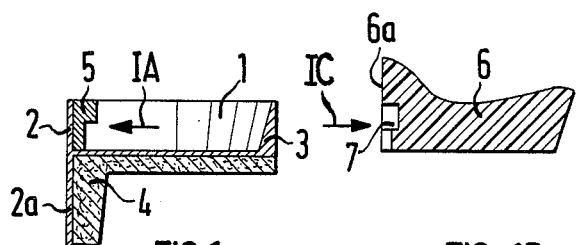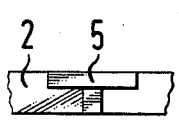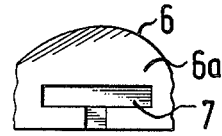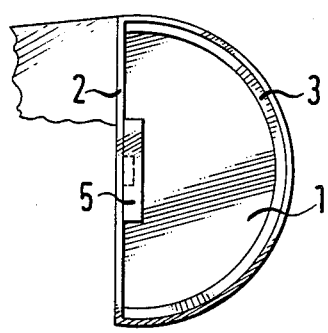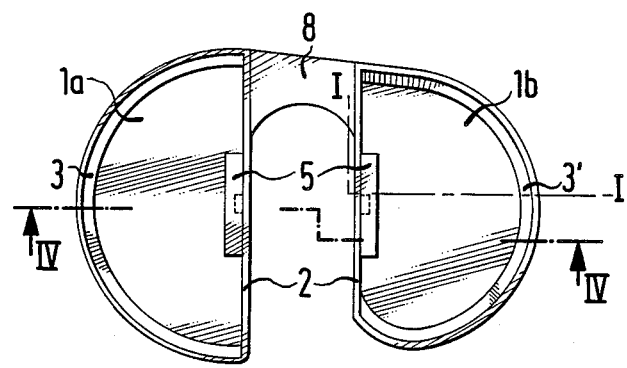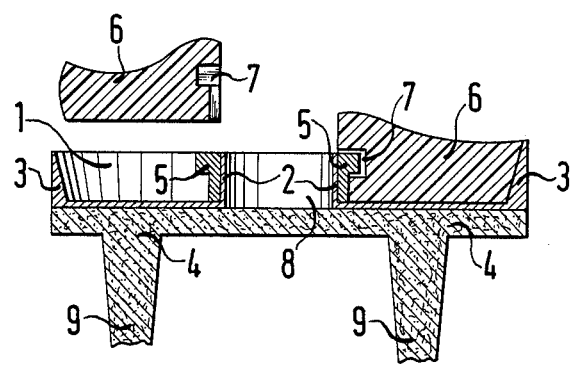

ANCHORAGE FOR TIBIA PLATES

BACKGROUND OF THE INVENTION

1. Field of the Invention

The invention relates to an anchorage for tibia plates of a knee joint endoprosthesis, the anchorage being disposed in the upper part of the skin bone, on both sides of a central web or ridge extending from the front of the knee joint to the rear thereof, and having planar side faces.

2. Description of the Prior Art

It is known to join tibia plates, having a base face to be anchored in the upper part of the skin bone, to one another by means of dovetail-like snap-in projections and recesses (German Offenlegungsschrift No. 2,550,704) or to join tibia plates to the shin bone by means of projections of dovetail-like cross-section in corresponding profiled-milled cuts in the bone (German Offenlegungsschrift No. 2,608,628). As has been found in practice, these known joints are not sufficiently stable, since anchorages with smooth faces do not make a good joint with the shin bone and profiled milled cuts of the shin bone are difficult to prepare and likewise do not appear to be sufficiently stable.

OBJECTS OF THE INVENTION

It is the object of the invention to obtain an irreleasable anchorage of the tibia prosthesis part in the upper part of the shin bone coupled with easy exchange or removal of the tibia plates consumed by wear.

According to the invention, this object is achieved, in the above-mentioned anchorage, as follows:

For each tibia plate of plastic material, a metal tray is provided which is fitted on the underside surface or base thereof with a metallic, open-cell coating or layer permitting the formation of bone tissue in the cells thereof.

The metal tray has a planar wall being adjacent to or attached to one of the planar side faces of the central web or ridge, as well as an arcuate side wall, the thickness of which increases or widens conically on the inside therof from the upper edge (or top) of the tray to the bottom or base thereof.

The planar wall is provided with a T-shaped projection on the inside surface thereof. The tibia plate, the outline or profile thereof matching the outline or profile of the inner face or surface of the tray, is provided with a planar side wall having a T-shaped recess facing and matching the T-shaped projection of the planar wall.

By means of this solution, the tray carrying the tibia plate will form an irreleasable joint with the corresponding prepared surface of the shin bone due to the open-cell coating or layer, provided on the underside thereof, as a result of bone tissue growing into the cells, with subsequent formation of bone.

On the other hand, due to the engagement of the T-shaped projection with the corresponding T-shaped recess of the tibia plate, and due to the profile of the tibia plate matching the cone-shaped profile of the arcuate side wall of the tray, the tibia plate can be held firmly in the tray by clamping. However, the tibia plate can be detached from the tray by lifting the plate peripheral part located on the outside of the tray by means of, for example, a pointed object or tool.

BRIEF DESCRIPTION OF THE DRAWINGS

The invention is explained below with further advantageous features by reference to the drawings in which embodiments of the invention are illustrated, and in which:

FIG. 1 is an elevation cross-sectional and partial side view of an anchorage of the present invention, taken along line I—I of FIG. 3.

FIG. 1A is a partial side view in the direction of arrow IA, of the embodiment of FIG. 1.

FIG. 1B is an elevation cross-sectional side view of the tibia plate of the present invention.

FIG. 1C is a partial side view, in the direction of arrow IC, of the tibia plate of FIG. 1B.

FIG. 2 is a plan view of the tray embodiment of FIG. 1.

FIG. 3 is a plan view of two anchorages of the present invention rigidly joined together.

FIG. 4 is an elevation cross-sectional side view of the embodiment of FIG. 3, taken along line IV—IV, showing, in addition, one separate tibia plate and another tibia plate inserted into one of the anchorages.

DETAILED DESCRIPTION OF THE PREFERRED EMBODIMENTS

According to the present invention, the anchorage for tibia plates of knee joint endoprostheses consists of a metal tray 1 (FIG. 1) provided with a planar side wall 2 standing perpendicular to the base of the tray and a side wall 3 in the form of a circular arc. The planar wall 2 of the tray bears against or adjoins one side face of a central web or ridge (known and, therefore, not shown) consisting, for example, of a bone part of the shin bone, with advantageously parallel planar side faces. The central web or ridge is rising or becoming broader from the front of the knee joint towards the rear thereof and vice versa. This wall 2 is provided at the base with a likewise planar extension 2a which, like the underside of the base of the tray (including lower webs thereof), is provided with a metallic, open-cell coating or layer 4, into the cells of which bone tissue can grow in with subsequent formation of bone, so that the tray 1 is thus joined to the shin bone with a virtually irreleasable connection.

The planar side wall 2 is provided on its inside surface (inside of the tray) with a T-shaped projection 5, the horizontal flanges of which (FIG. 1a) end with the upper edge of the tray and the web of which points downwards. The thickness of the arcuate side wall 3 on the inside of the tray increases conically from the top downwards to the base of the tray, as FIG. 1 shows.

The tray 1 serves to carry a tibia plate 6 of plastic material, which is provided with an upper slide surface for members of a femur part and a cone-shaped outline or profile which matches the outline conical or profile of the inner face or surface of the tray. This plate (FIGS. 1b and 1c) is also provided with a flat base and a planar side wall 6a perpendicular to the base and with a T-shaped recess 7 which faces and matches the projection 5.

To join the tibia plate to the tray 1, it is introduced in an angled or inclined position into the tray 1, so that the T-shaped projection 5 engages with the T-shaped recess 7 of the tibia plate. The tibia plate 6 is then forced into the tray 1 by pressure from above, an internal stress being exerted by the cone-shaped arcuate side wall 3 upon the plate 6, whereby the plate is definitely and firmly affiixed or attached to the tray 1. When wear of the tibia plate 6 occurs, the tip of an instrument is applied to the peripheral part of the plate projecting from the tray 1 and located opposite the wall 2, and the plate can then be tilted by upward pressure into a position angled (at an oblique angle) relative to the base of the tray, so that the engagement of the T-shaped projection 5 with the T-shaped recess 7 can also be released. A new plate can then be introduced again into the tray 1 which remains rigidly joined to the shin bone.

It is also possible to join the two trays 1a and 1b according to FIGS. 3 and 4, the trays to be anchored on both sides of the central web or ridge and generally being mirror images or substantially similar. A double tray unit can be formed by rigidly joining the planar walls 2 of the trays in the front region thereof by means of a metal bridge 8 connecting one tray to another. However, in other respects, the trays 1a and 1b are shaped in the way described by reference to FIGS. 1 and 2. In this case, it is preferable and more advantageous to provide the open-cell base coating or layer 4 with anchorage spikes or pins 9 which advantageously assume an oblique or inclined position relative to the base of the tray, with an inclination from the front rearwards.

In general, the open-cell anchorage coating or layer 4 is joined to the base of the tray 1 or of the trays 1a and 1b at high temperatures by fusion welding.

The invention and many of its attendant advantages will be understood from the foregoing description, and it will be apparent that various changes may be made in the form and construction and arrangement of the parts described, without departing from the spirit and scope of the invention or sacrificing all of its material advantages, the form described merely being a preferred embodiment thereof.

What is claimed is:

1. An anchorage for plastic tibia plates of a knee joint endoprosthesis, said anchorage disposed in an upper part of a shin bone on both sides of a central web or ridge therof extending from the front of the knee joint towards the rear thereof, said central web or ridge having parallel planar side faces, said anchorage comprising a metal tray for carrying a tibia plate, the tray being provided on the base thereof with a metallic open-cell layer permitting growth of bone tissue into the cells thereof, and the tray having a planar wall perpendicular to the base thereof and bearing against one of said planar side faces of the central web or ridge, which planar wall is provided on the inside surface thereof with a T-shaped projection, and a cone-shaped arcuate side wall the thickness of which increases conically on the inside of the tray from top to bottom of the tray, the tibia plate having a conical profile that matches the profile of the inner surface of the tray and being provided with a flat base and a planar side wall perpendicular to the flat base and having a T-shaped recess facing and matching the T-shaped projection of said planar wall of the tray, the tibia plate being engageable with the tray so that the tibia plate can be firmly and detachably fitted into the tray of said anchorage.

2. An anchorage as claimed in claim 1, wherein the T-shaped projection of the planar wall of the tray is provided with horizontal flanges which end at an upper edge of said planar wall of the tray and a web which points downwardly thereof.

3. An anchorage as claimed in claim 1, wherein said planar wall of the tray extends downwards beyond the tray base and is provided on the outer surface thereof with a metallic open-cell layer.

4. An anchorage as claimed in claim 1, further comprising two substantially similar metal trays, each of which having a planar wall bearing against a respective one of said planar side faces of the central web or ridge, and a bridge rigidly joining the two trays at a front end thereof with their planar walls facing one another, the trays being provided on the underside layer thereof with metallic open-cell pins disposed in an inclined position relative to the base of the tray.

* * * * *